United States Patent [19]

Knollenberg

[11] Patent Number: 4,571,079
[45] Date of Patent: Feb. 18, 1986

[54] AEROSOL SAMPLING DEVICE AND METHOD WITH IMPROVED SAMPLE FLOW CHARACTERISTICS

[75] Inventor: Robert G. Knollenberg, Boulder, Colo.

[73] Assignee: Particle Measuring Systems, Inc., Boulder, Colo.

[21] Appl. No.: 566,863

[22] Filed: Dec. 29, 1983

[51] Int. Cl.$^4$ .................... G01N 15/02; G01N 21/00
[52] U.S. Cl. ......................... 356/336; 356/36; 356/339
[58] Field of Search ............... 356/335, 336, 337, 36, 356/339; 239/133, 134, 135, 139; 73/25

[56] References Cited

U.S. PATENT DOCUMENTS

| | | | |
|---|---|---|---|
| 2,643,541 | 6/1953 | McCreary | 73/25 |
| 3,406,289 | 10/1968 | Schleusener | 356/335 |
| 3,835,294 | 9/1974 | Krohn et al. | 219/305 |

*Primary Examiner*—John E. Kittle
*Assistant Examiner*—Thomas C. Saitta
*Attorney, Agent, or Firm*—O'Rourke & Harris

[57] ABSTRACT

An aerosol sampling device and method are disclosed having improved sample flow characteristics. Sample flowing through an inlet nozzle is heated prior to discharge from the nozzle toward a measurement area to maintain sample flow more nearly laminar by compensating for the adiabatic cooling that occurs due to acceleration of flow through the nozzle. In addition, heating of the sample flow prevents condensation which can result with ambient air having a relative humidity of fifty percent. An optical particle measuring apparatus is shown having a generator for providing a laser beam, the path of which is through a measurement area, and an inlet nozzle through which aerosol sample is injected into the measurement area, after heating in accordance with this invention, to allow operation of the laser at a relatively high Q by reducing non-laminar flow characteristics.

18 Claims, 7 Drawing Figures

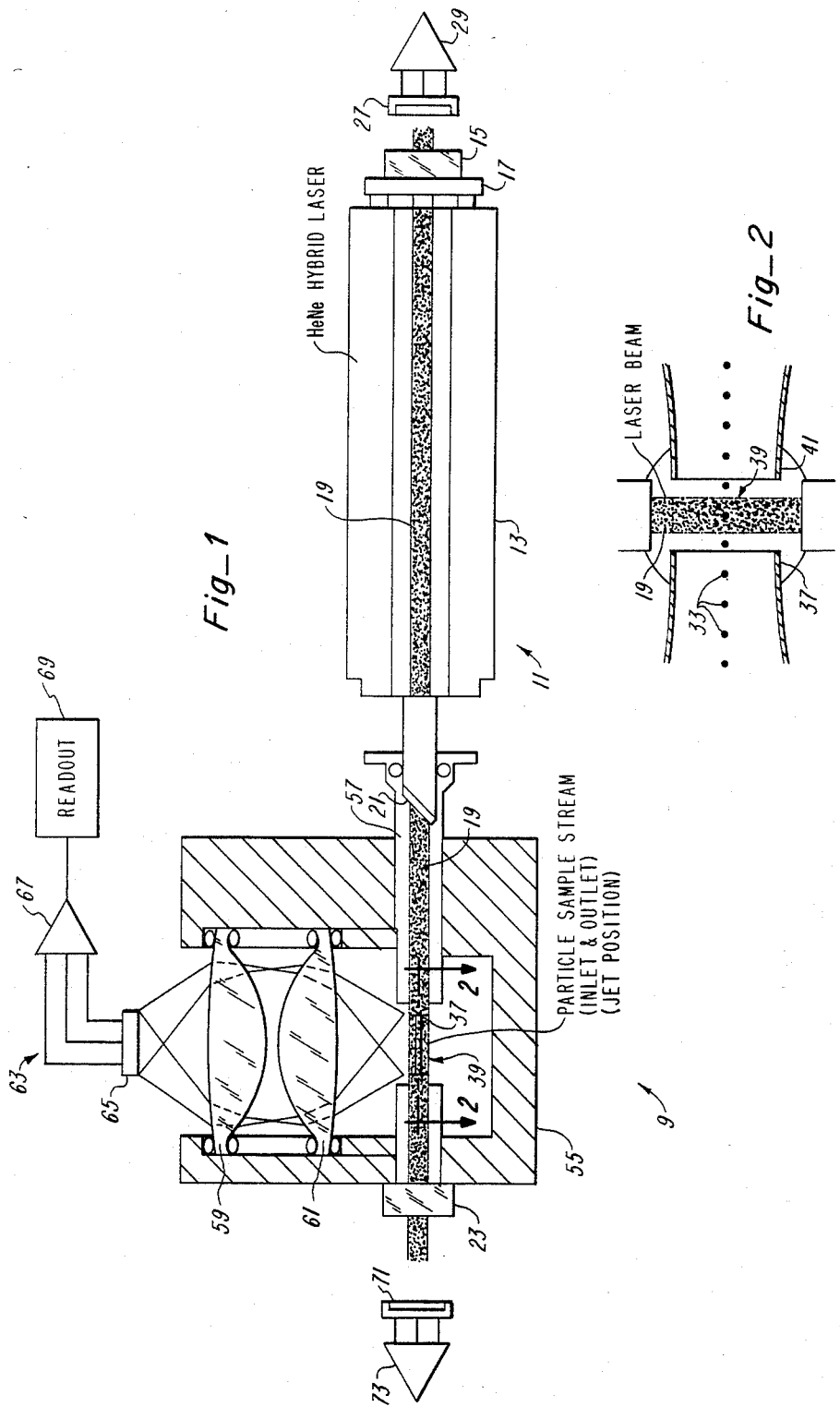

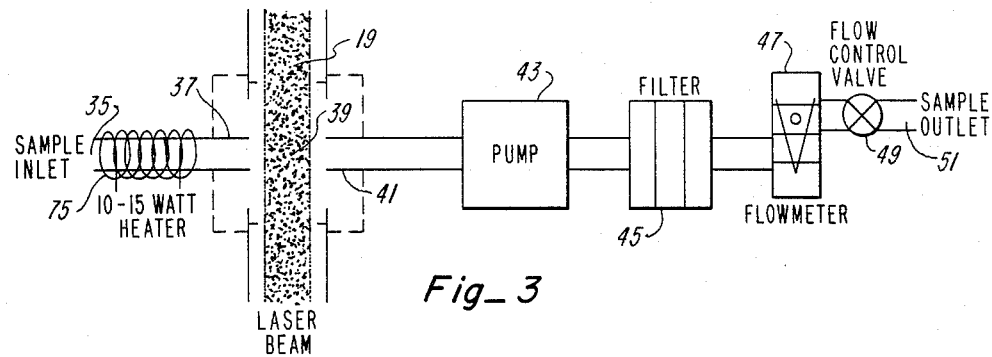
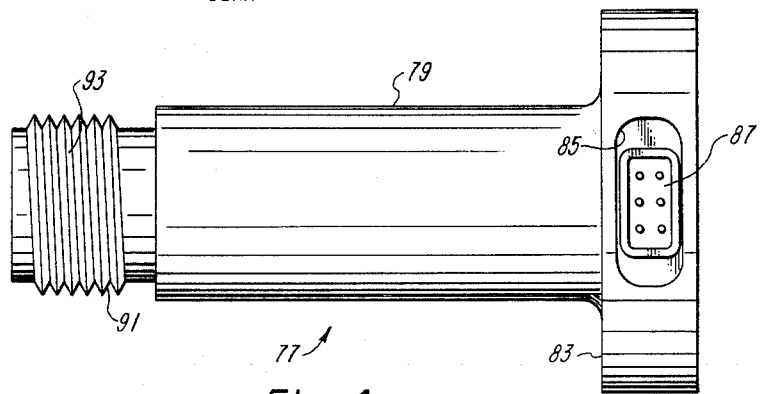
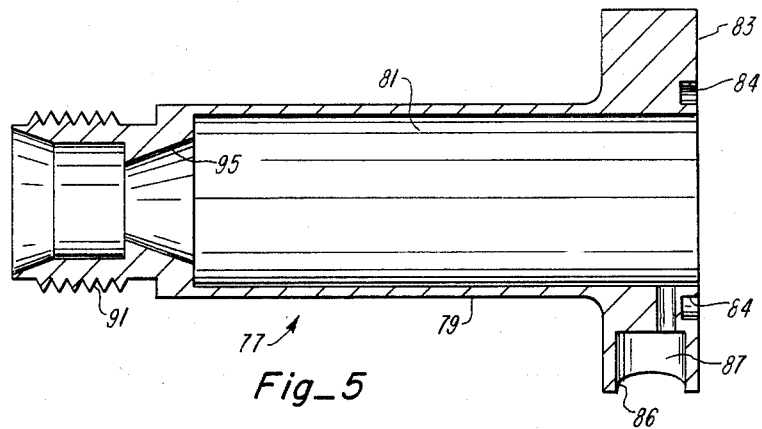
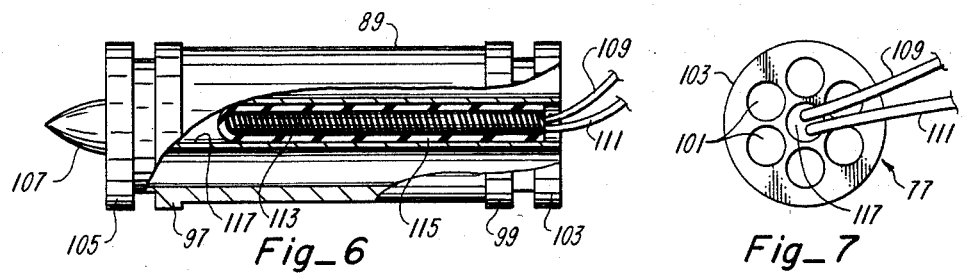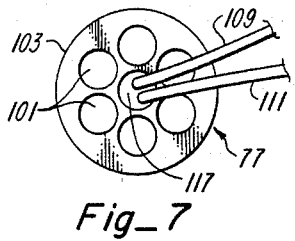

AEROSOL SAMPLING DEVICE AND METHOD WITH IMPROVED SAMPLE FLOW CHARACTERISTICS

FIELD OF THE INVENTION

This invention is directed to flow characteristic improvement, and, more particularly, is directed to an aerosol sampling device and method having improved sample flow characteristics due to sample heating.

BACKGROUND OF THE INVENTION

The desirability of sampling of flowing material for various purposes is well known, and such devices for such a purpose have been heretofore suggested and/or utilized. Utilization of a sampling device in particle measuring systems for optical sizing purposes is also now known, and such an optical particle measuring system is shown, for example, in U.S. Pat. No. 3,406,289.

It has been found that where a flow path includes a flow restriction, such as a nozzle or jet, the resulting increase in acceleration in flow through the inlet results in adiabatic cooling which adversely affects laminar flow. For sample flow through a nozzle in an optical particle measuring apparatus of the type having an open cavity laser, it has been found that the laser operates at a lower cavity Q (the ratio of the resonant energy density inside a laser cavity to all possible losses is referred to as the "Q" of the cavity) due to non-laminar flow characteristics since open cavity devices are very sensitive to such flow characteristics.

SUMMARY OF THE INVENTION

This invention provides improved flow characteristics, and provide an aerosol supply device and method having improved sample flow characteristics. By heating sample prior to discharge from a nozzle, more nearly laminar flow is achieved by compensating for the adiabatic cooling of the sample as the sample flows through the restriction imposed by the nozzle. In addition, heating of the sample flow prevents condensation which can result with ambient air having a relative humidity of fifty percent. Incorporated in a particle measuring apparatus that includes an open cavity laser beam generator, operation of the laser at a relatively high cavity Q is achieved by providing more nearly laminar flow characteristics for the sample.

It is therefore an object of this invention to provide a device having improved flow characteristics and a method for achieving such flow characteristics.

It is another object of this invention to provide an improved aerosol sampling device and method.

It is another object of this invention to provide an improved aerosol sampling device and method having improved sample flow characteristics.

It is still another object of this invention to provide an aerosol sampling device and method having improved sample flow characteristics achieved by sample heating prior to utilization.

It is still another object of this invention to provide an improved aerosol sampling device and method that includes sample heating prior to discharge through a nozzle to a utilization area to compensate for adiabatic cooling of the sample in flowing through the nozzle.

It is yet another object of this invention to provide an improved aerosol sampling device and method that includes sample heating prior to discharge through a nozzle to a utilization area to prevent condensation.

It is yet another object of this invention to provide an improved optical particle measuring device and method that allows operation of the laser of the device at a relatively high Q.

With these and other objects in view, which will become apparent to one skilled in the art as the description proceeds, this invention resides in the novel construction, combination, arrangement of parts and method substantially as hereinafter described and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which:

FIG. 1 is a side section view schematic presentation of a particle measuring system having the device and method of this invention incorporated therein;

FIG. 2 is a partial cross-sectional depiction taken along lines 2—2 of FIG. 1 showing sample discharge through a nozzle into the measurement area;

FIG. 3 is a schematic view illustrating sample flow through the measurement area and showing sample heating according to this invention;

FIG. 4 is a side view of the heater assembly shown in FIG. 3;

FIG. 5 is a cross-sectional view of the heater assembly shown in FIG. 4 but rotated 90° with respect thereto;

FIG. 6 is a side view of the heating element incorporated into the heating assembly shown in FIGS. 4 and 5; and FIG. 7 is an end view of the heating element shown in FIG. 6.

DESCRIPTION OF THE INVENTION

While not meant to be limited thereto, this invention is particularly well suited for use with a particle measuring system of the type wherein sample is discharged from a nozzle to a measuring area which also has a laser beam directed therethrough. Lasers are basically resonant cavity devices and open cavity lasers have been found to be useful for generating the measuring laser beam.

An optical system for a particle measuring device 9 is shown in FIG. 1. As shown, open cavity laser 11 (typically a HeNe laser) includes a plasma tube 13 having a curved mirror 15 positioned at one end by mirror mount 17, with the generated laser beam 19 being transmitted from the cylinder through Brewster's window 21 to external mirror 23.

A photodetector 27 and preamplifier 29 are conventionally positioned along the laser beam axis outside mirror 15 to provide a measure of relative intensity of illumination.

As shown best in FIGS. 1 through 3, for particle size measurement, fluid, such as aerosol, with particles 33 to be size measured therein, is introduced through sample inlet 35 and coupled to jet, or nozzle, 37 (as indicated best in FIG. 2) and discharged therefrom so that the particles pass through measurement area 39 (and thus also through laser beam 19 between Brewster's window 21 and external laser mirror 23) before reaching discharge port 41. Particles 33 are therefore injected into the measurement area in a direction normal to the laser beam path.

As shown in FIG. 3, the sample collected at port 41 is propelled by pump 43 through filter 45, flowmeter 47 and flow control valve 49 to sample outlet 51.

As shown in FIG. 1, a sample block 55 is positioned above the particle measurement area with coupling tube 57 being provided to allow laser beam 19 to pass through measurement area 39 to mirror 23. As shown, block 55 positions light collecting optical elements, such as a pair of aspheric lenses 59 and 61, above and close to measurement area 39.

A scattering photodetector module 63 is positioned adjacent to block 55, and module 63 includes photodiode 65, conventionally located in the focal plane of lenses 59 and 61, and an amplifier 67. The output from scattering photodetector module 63 is coupled to readout 69 (which may be an oscilloscope, for example).

Photodetector 71 and preamplifier 73 may be optionally positioned along the laser beam axis at the other side of mirror 23 to provide a reference measurement as does photodetector 27 and preamplifier 29.

Particles of a few microns and smaller introduce negligible cavity losses requiring that particle detection and sizing be performed utilizing particle light scattering received by the scattering photodetector module 63, while larger particles produce easily measurable losses of energy via monitoring extinction of output power observable at either reference detector 27 or 71.

It has been found, however, that where jets, or nozzles, are utilized, the flow restrictions introduced by such devices cause adiabatic cooling due to acceleration of flow through the nozzle restriction, and this results in a non-laminar flow. Since open cavity laser devices are very sensitive to non-laminar flow characteristics, the cavity Q is reduced. Adiabatic cooling can also result in condensation of small droplets. Such droplets are not present in ambient air and are thus a measurement artifact.

This invention improves sample flow characteristics by heating the sample prior to injection into the measurement area. By heating the sample by an amount equivalent to the adiabatic cooling occuring due to acceleration of flow through the inlet nozzle, a more nearly laminar flow is achieved. When utilized in conjunction with an open laser cavity as shown in FIG. 1, the use of a heater to warm the sample prior to discharge into the measurement area has been found to allow operation of the laser at a higher cavity Q by as much as a factor of ten.

As indicated in FIG. 3, heating is accomplished by a 10 to 15 watt heater 75 positioned between the sample inlet 35 and nozzle 37. A sample injection assembly 77, which includes sample inlet 35, heater element 89, and nozzle 37, is shown in greater detail in FIGS. 4 through 7.

As shown, injection assembly 77 includes an outer cylinder 79 having a central bore 81 therein. A mounting flange 83 is integrally formed at one end of cylinder 79, and flange 83 may have mounting apertures (not shown) therein and preferably also includes at the back face, a circular indentation 84 for sealing at the sample inlet.

An oval shaped indentation 85 is formed in the periphery of flange 83 to receive the female portion of an electrical connector plug 87 for supplying electrical power to heater element 89 which is positioned within central bore 81. As shown in FIG. 4, the nozzle end 91 of cylinder 79 has a reduced outer diameter with threads 93 thereon to adapt the injection assembly for positioning adjacent to the measurement area for sample injection.

As shown in FIG. 5, central bore 81 is tapered by means of cone-shaped wall 95 near end 91 to thus constitute a jet, or nozzle, of restricted diameter.

As shown in FIG. 6, cylindrical heater element 89 has positioning shoulders 97 and 99 at opposite end portions which engage the walls of bore 81 of cylinder 79. As shown in FIG. 7, heater element 89 has a series of spaced bores 101 extending therethrough (six bores are shown), which bores also extend through hub spacer 103 and front spacer 105. Spacer 105 also has a cone-shaped tip 107 positioned adjacent to cone-shaped walls 95 at the nozzle. Wires 109 and 111 are connected between the female portion of plug 87 and heater unit 113 (which can be, for example, an insulated wire coil encapsulated in insulation layer 115) with heater unit 113 fitting in central bore 117 of heater element 89 so that the heating element supplies heat to sample flowing through bores 101 when electrical power is supplied to the element.

In operation, the heater element is positioned between the sample inlet and nozzle (which can be accomplished by using an injection assembly as brought out hereinabove), and heat is applied (from a conventional 115 volt 60 Hz power supply, for example) to offset the temperature drop which occurs during the adiabatic expansion of sample exiting the restricted inlet jet. Sample is then directed through the laser beam at the measurement area (at a sample rate of 500 cm$^3$/sec, for example) and the measurement is optically effected. By thus heating the sample, the temperature of the aerosol sample at the point of measurement is caused to be the same as the ambient air and this results in more nearly laminar flow which permits operation of the laser at a higher cavity Q than would otherwise be possible.

As can be appreciated from the foregoing, this invention provides a device with improved sample flow characteristics and a method for effecting improved flow characteristics, both of which are achieved through heating of sample prior to discharge from a nozzle.

What is claimed is:

1. In an aerosol sampling apparatus having a laser device with a measuring area in the laser cavity, laser means for generating a laser beam and directing said beam through said measuring area and a restricted inlet through which aerosol to be sampled is introduced into said measuring area, a flow improvement device comprising:

heating means adjacent to said restricted inlet and acting on said aerosol flowing through said restricted inlet so that said aerosol is heated sufficiently to thereby enhance laminar flow of said aerosol through said device to thereby allow operation of said laser means at a higher Q when said aerosol is heated than would otherwise be possible with said aerosol unheated and under like conditions as when heated.

2. The device of claim 1 wherein said heating means includes a heating element in the flow path of said aerosol passing through said restricted inlet.

3. The device of claim 2 wherein said heating element is an electrical heating element, and wherein said heating means includes means for supplying electrical energy to said heating element.

4. The device of claim 3 wherein said heating element utilizes about 10 to 15 watts of power.

5. The device of claim 1 wherein said heating means heats said aerosol by an amount about equivalent to the adiabatic cooling arising from acceleration of flow of said aerosol through said restricted inlet.

6. The device of claim 1 wherein said heating means heats said aerosol sufficiently so that said Q factor is increased by a factor of about 10.

7. An improved particle measuring system, comprising:
   means defining a measuring area within the cavity of a laser device;
   laser beam generating means providing a laser beam at said measuring area;
   sample inlet means;
   sample directing means connected with said sample inlet means for directing said sample from said sample inlet means through said measuring area, said sample directing means including nozzle means having a restricted area opening therein with said nozzle means being positioned to direct sample flow to said measuring area; and
   heating means positioned adjacent to said nozzle means for heating sample flowing from said sample inlet means to said nozzle means to offset the temperature drop which occurs during adiabatic expansion of sample in passing through said restricted area of said nozzle means so that said sample directed to said measuring area is substantially unaffected by said restricted area of said nozzle means to thus improve performance of the laser beam generating means.

8. The system of claim 7 wherein said heating means is a heating element positioned in the path of sample flowing from said sample inlet means to said nozzle means.

9. The system of claim 8 wherein said sample directing means includes a conduit through which sample is directed from said sample conduit means, and wherein said heating element is positioned within said conduit.

10. The system of claim 9 wherein said heating element is an electrical heating element, and wherein said heating means includes means for supplying electrical energy to said heating element.

11. The system of claim 9 wherein said heating element has a tip portion positioned adjacent to said restricted area of said nozzle means.

12. The system of claim 7 wherein said heating means heats said sample by an amount about equivalent to the adiabatic cooling arising from acceleration of flow through said nozzle means so that the temperature of the sample at the measuring area is substantially the same as ambient air.

13. The system of claim 7 wherein said heating means heats said sample sufficiently to permit operation of said laser beam generating means at a higher Q than would otherwise be possible with said sample unheated and under like conditions as when heated.

14. The system of claim 13 wherein said heating means heats said sample sufficiently so that the laser beam generating means is operated at a Q that is increased by a factor of about ten.

15. The system of claim 7 wherein said sample inlet means, said sample directing means, and said heating means are mounted in a common mounting assembly.

16. A method for improving flow characteristics of a fluid sample flowing through a restricted inlet to a measuring area within the cavity of a laser device which also receives a laser beam from a laser the efficiency of operation of which is dependent at least in part on the temperature relationship of the sample to ambient air, said method comprising:
   heating said fluid sample prior to introduction into said restricted inlet with said heating being sufficient to compensate for the adiabatic cooling arising from acceleration of flow of sample through said restricted inlet so that said sample when at said measuring area is substantially unaffected by passing through said restricted inlet to thereby enhance laser performance.

17. The method of claim 16 wherein said heating is sufficient to result in a more nearly laminar flow of fluid than would otherwise occur in the absence of such heating.

18. A method for improving flow characteristics of aerosol flowing through a nozzle to a measuring area within the cavity of a laser device in a particle measuring system having laser beam generating means for providing a laser beam to said measuring area, said method comprising:
   heating of said aerosol prior to introduction into said measuring area to thereby enhance laminar flow and thereby enable operation of said laser at a higher Q when said aerosol is heated than would otherwise be possible with said aerosol unheated and under like conditions as when heated.

* * * * *